United States Patent [19]

Manley et al.

[11] Patent Number: 5,435,436
[45] Date of Patent: Jul. 25, 1995

[54] THERMOMECHANICALLY INTEGRATED DISTILLATION OF CLOSE-BOILING LIGHT HYDROCARBONS

[76] Inventors: David B. Manley, 32 Cedar Grove Rd., Rolla, Mo. 65401; Dominic G. Greene, 5000 Cedar Plaza Pky., St. Louis, Mo. 63128

[21] Appl. No.: 184,269

[22] Filed: Jan. 21, 1994

[51] Int. Cl.$^6$ ............................ B01D 3/06; F25J 3/02
[52] U.S. Cl. .......................................... 203/74; 62/24; 62/34; 62/510; 202/172; 202/186; 203/80; 203/87; 203/88; 203/DIG. 9; 203/99; 203/DIG. 19; 208/351; 208/364
[58] Field of Search ...................... 203/74.1, 75, 78, 88, 203/87, 91, 80, 99, DIG. 9, DIG. 19, DIG. 4; 62/24, 11, 34, 40, 498, 524, 510; 208/351, 352, 354, 364, 355; 202/172, 186

[56] References Cited

U.S. PATENT DOCUMENTS

| | | | |
|---|---|---|---|
| 3,783,126 | 1/1974 | Hayward et al. | 208/351 |
| 3,813,890 | 6/1974 | Bligh | 62/40 |
| 4,167,402 | 9/1979 | Davis | 62/28 |
| 4,738,699 | 4/1988 | Apffel | 62/24 |

OTHER PUBLICATIONS

King, *Separation Processes*, 2nd Edition, McGraw-Hill Book Company, New York, pp. 692–710, at 702 (1980).
Kniel et al., *Ethylene, Keystone to the Petrochemical Industry*, Marcel Dekker, Inc., New York, Chapter 7, at pp. 98–100 (1980).
Howat III et al., "A New Correlation of Propene-Propane Vapor-Liquid Equilibrium Data and Application of the Correlation to Determine Optimum Fractionator Operating Pressure in the Manufacture of Polymerization-Grade Propene," *Industrial Engineering Chemical Process Des. Dev.*, vol. 19, No. 2, pp. 318–323 (1980).
Sage et al., "System 1-Butene-n-Butane," *Industrial and Engineering Chemistry*, pp. 1299–1301, 1948.
Barclay et al., "Relative Volatilities of the Ethane–Ethylene System from Total Pressure Measurements," *Journal of Chemical Engineering Data*, vol. 27, pp. 135–142, 1982.
Greene, *Thermomechanically Integrated Distillation of Ethylene from Ethane*, Thesis, University of Missouri, Presented 1992 (Unpublished).

Primary Examiner—Virginia Manoharan
Attorney, Agent, or Firm—Daniel N. Lundeen

[57] ABSTRACT

A thermomechanically integrated distillation column and method for the separation of ethylene from ethane and other close-boiling light hydrocarbons. The column has a plurality of sections operated at successively lower pressures from a high pressure subcritical section to a superatmosphere bottoms product zone. Bottoms liquid from the high pressure and intermediate sections are flashed in respective cooling loops to about the pressure of the section of next lower pressure, vaporized in heat exchange with an overhead condensing zone and introduced to the top stage of next lower pressure section. Vapor from the intermediate sections and the bottoms product zone are compressed in respective compression loops and fed to the bottom stage of the section of the next higher pressure. External refrigerant can be supplied to the overhead condensing zone for trim as needed for control purposes.

23 Claims, 4 Drawing Sheets

THERMOMECHANICALLY INTEGRATED DISTILLATION OF CLOSE-BOILING LIGHT HYDROCARBONS

FIELD OF THE INVENTION

The present invention relates to a method for separating close-boiling light hydrocarbons. More particularly, the present invention relates to art ethylene purification process using thermomechanically integrated distillation of ethylene from ethane to achieve energy and capital equipment cost savings.

BACKGROUND OF THE INVENTION

Close-boiling light hydrocarbon mixtures with positive deviations from ideal solution behavior, such as ethylene/ethane, propylene/propane, and 1-butylene/n-butane, are normally distilled to highly purify the more volatile olefin component to satisfy downstream processing requirements. See Barclay et al., "Relative Volatilities of the Ethane-Ethylene System from Total Pressure Measurements," *Journal of Chemical Engineering Data*, Vol. 27, No. 2, pp. 135–142 (1982); Howat III et al., "A New Correlation of Propene-Propane Vapor-Liquid Equilibrium Data and Application of the Correlation to Determine Optimum Fractionator Operating Pressure in the Manufacture of Polymerization-Grade Propene," *Industrial Engineering Chemical Process Des Dev.*, Vol. 19, No. 2, pp. 318–323 (1980); and Sage et al., "System 1-Butene-n-Butane, Composition of Coexisting Phases," *Industrial Engineering Chemical Process Des. Dev.*, Vol. 40, pp. 1299–1301 (1948). The vapor-liquid equilibria for mixtures like these lead to distillation conditions with high reflux ratios where heat pumping and interreboiling can be combined in economically advantageous ways. As an example, an ethylene/ethane separation is normally a step at the end of a low temperature process for the separation of hydrocarbons, e.g. in the recovery of ethylene from the effluent of a pyrolysis cracking furnace.

It is known that ethylene can be separated from ethane by conventional distillation with an externally heated reboiler and an externally cooled condenser. See Kniel et al., *Ethylene, Keystone to the Petrochemical Industry*, Marcel Dekker, Inc., New York, Chapter 7, at pp. 98–100 (1980). A disadvantage of this process is that, because of the isobaric composition dependence of the relative volatility of ethylene to ethane (see FIG. 3), and because no interreboiler is used, the stripping section operates at an internal reflux ratio much higher than necessary. Another disadvantage is that separate condensing and reboiling heat exchangers must be used to exchange heat individually with the respective external cooling and heating mediums.

It is also known that ethylene can be separated from ethane using conventional distillation with an externally heated interreboiler. See King, *Separation Processes*, 2nd Edition, McGraw-Hill Book Company, New York, pp. 692–710, at 702 (1980). A disadvantage of this process is that separate condensing, interreboiling, and reboiling heat exchangers must be used to individually exchange heat with the external cooling and heating mediums.

It is also known that ethylene can be separated from ethane using interreboiled distillation with heat pumping where the working fluid is the overhead vapor, an external fluid, or the reboiler liquid. See King, at page 696. This process has different disadvantages depending on the choice of the working fluid. When the working fluid is the overhead vapor, the column pressure must be low enough to avoid approaching critical conditions in the reboiler, thus requiring expensive alloy steel construction of the column and compressor; and, under these conditions, the product ethylene must be cooled to excessively low temperatures. When the working fluid is the overhead vapor, the ethylene product can also become contaminated by process leaks in the heat pump circuit. When the working fluid is an external fluid, separate condensing, interreboiling, and reboiling heat exchangers must be used to individually exchange heat with the external working fluid. When the working fluid is the reboiler liquid, heat absorbed by the interreboiler from the overhead vapor must be transferred indirectly through the working fluid.

It is also known that ethylene can be separated from ethane using multieffect distillation. See King, at pages 694 and 697–700. A disadvantage of this process is that, because no interreboilers are used, the stripping sections operate at internal reflux ratios much higher than necessary. Another disadvantage is that two or more tall distillation columns are required. Another disadvantage is that, because of the low pressure and temperature, at least one column and one heat exchanger must be constructed of expensive alloy steel. Another disadvantage is that, because of the large temperature difference from the low pressure condenser to the high pressure reboiler, conventional heat pumping is not practical.

It is also known that ethylene can be separated from ethane using a dual pressure fractionation tower. See Hayward, U.S. Pat. No. 3,783,126. A disadvantage of this process is that, because no interreboiler is used, the stripping section operates at an internal reflux ratio much higher than necessary. Another disadvantage is that, because heat pumping is not used, separate condensing and reboiling heat exchangers are used to exchange heat with the respective external cooling and heating mediums.

It is also known that ethylene can be separated from ethane using secondary reflux and vaporization where the stripping and enriching sections are at different pressures, allowing heat to be directly exchanged between individual plates in the stripping section and individual plates in the enriching section. See King, at pages 707–708. A disadvantage of this process is that, because the relative volatility of ethylene to ethane is significantly greater in the stripping section than in the enriching section, the temperature differences between the individual plates exchanging heat are not uniform, thus requiring a large pressure difference between the two sections with associated large compression costs. Another disadvantage is that, because of the isobaric composition dependence of the relative volatility of ethylene to ethane, intercondensing heat exchange cannot be used effectively in the enriching section.

And, it is also known from King, at pages 708 and 710, that ethylene can be separated from ethane using isothermal distillation where vapors from each stage are compressed and cooled before being fed to the stage above. A disadvantage of this process is that a large number of compression stages are necessary with associated large o capital costs.

SUMMARY OF THE INVENTION

The present invention provides a distillation process for the separation of close-boiling light hydrocarbons such as ethylene from ethane where no section of the column needs to operate at an internal reflux ratio excessively above minimum, where open loop heat pumping can be used without requiring expensive alloy steel construction and without risking contamination of the overhead product, where sensible heating and cooling effects are reduced by approaching isothermal operation, and/or where the number of pieces of process equipment such as compressor stages, column sections, heat exchangers, pumps, drums, valves etc. is not excessive. As a result, the present distillation achieves relatively high thermodynamic efficiency and relatively low operating and capital costs.

In one aspect, the present invention provides distillation apparatus for separating close-boiling light hydrocarbons such as ethylene/ethane, propylene/propane, 1-butylene/n-butane, and like mixtures. The apparatus includes a high pressure section at subcritical pressure having high and low temperature stages, a bottoms product zone at superatmospheric pressure, an intermediate section comprising one or more intermediate zones of successively lower pressure from the high pressure section to the bottoms product zone, and high and low temperature stages in each of the intermediate zones. A feed zone is in fluid communication with at least one of the high pressure and intermediate sections for receiving a mixture of hydrocarbons including a light component and a heavy component. An overhead condensing zone is provided adjacent the low temperature (generally uppermost) stage of the high pressure section for condensing the light component at a condensation temperature thereof. A plurality of cooling loops are provided to effect condensation in the condensation zone. Each cooling loop includes an expansion valve for flashing fluid (generally liquid), from a respective high temperature (generally lowermost) stage, into a respective coolant supply line at a temperature below the condensation temperature of the condensing zone, through the condensing one in heat exchange therewith, and into respective coolant return lines. The coolant return lines introduce fluid of similar pressure into the low temperature stage of each respective intermediate, zone and into the bottoms product zone. A plurality of compression loops are provided for compressing fluid (generally vapor) from the respective bottoms product zone and the low temperature stage of each intermediate zone and discharging the compressed fluid to a respective high temperature stage of similar pressure. A line is provided for taking off light-component product of reduced heavy-component content from adjacent the condensing zone, and another line for taking off heavy-component product of reduced light-component content from the bottoms product zone.

The feed zone is preferably adjacent the high temperature stage of the high pressure section, or adjacent the low temperature stage of the intermediate zone having the highest pressure. Where the feed zone is disposed in the high pressure section, one or more stripping stages are preferably interposed between the feed zone and the high temperature stage of the high pressure section. If desired, a cooling loop for controllably circulating an external coolant through the condensing zone can be provided. The intermediate section preferably consists of one or two intermediate pressure zones. In one preferred embodiment, the light component product line is a side-draw at least two theoretical stages below a take-off line from a pasteurization zone for removing components more volatile than the light component product.

In another aspect, the invention provides a method for distilling ethylene from ethane, for example, which comprises feeding a mixture thereof to the feed zone of the distillation apparatus just described, and operating the apparatus to recover substantially purified ethylene in the light component product line, and substantially purified ethane in the heavy component product line.

In another aspect, the present invention provides a method for separating close-boiling light hydrocarbons such as ethylene/ethane, propylene/propane, 1-butylene/n-butane, and like mixtures by fractional distillation. The method includes the steps of: (a) supplying a mixture of hydrocarbons to a feed zone of a distillation unit having a high pressure section at subcritical pressure, an intermediate section including one or more intermediate zones of a successively lower pressure from the high pressure section to a bottoms product zone at superatmospheric pressure, wherein the high pressure section and the intermediate zones each have high and low temperature stages and the high pressure section has an overhead condensing zone adjacent the low temperature stage thereof; (b) condensing a light component in the condensing zone in heat exchange against a plurality of relatively cooler fluid streams expanded from the high temperature stages; (c) introducing the expanded fluid streams from step (b) to the respective low temperature stages in the intermediate and bottoms product zones having about the same pressure as the respective fluid stream from step (b); (d) compressing fluid streams from the bottoms product zone; and the low temperature stage of each intermediate zone; (e) introducing the compressed fluid streams from step (d) to the respective high temperature stages in the intermediate and high pressure sections having about the same pressure as the respective compressed fluid stream from step (d); (f) recovering a light-component stream adjacent the condensing zone having a reduced heavy-component content; and (g) recovering a heavy-component stream adjacent the bottoms product zone having a reduced light-component content.

In the method of the invention, the feed zone is preferably adjacent the high temperature stage of the high pressure section, usually with one or more stripping stages interposed between the feed zone and the high temperature stage of the high pressure section. If desired, the feed zone can also be disposed adjacent the low temperature stage of the intermediate zone which receives fluid expanded from the high temperature stage of the high pressure section, i.e. the intermediate zone having the highest pressure. To facilitate process control, the method can include condensing a portion of the light component in controllable heat exchange against an external coolant or refrigerant. The intermediate section of the distillation unit preferably comprises one or two intermediate zones. The fluid streams expanded in step (b) preferably comprise liquid, the fluid introduced in step (c) vapor, and the fluid streams compressed in step (d) vapor. Where the hydrocarbon mixture contains a minor amount of a volatile component, the method can include the further steps of recovering the light component stream in step (f) as a side-draw and removing the volatile component from a pasteurizing zone two or more theoretical stages above the side-draw.

Accordingly, the present invention thus provides a distillation column and methodology wherein the low temperature stages in the intermediate zones and the bottom product zone are at temperatures below that of the overhead condensing zone. Liquids from the high temperature stages in the intermediate and high pressure sections can be flashed through valves to the approximate pressure and temperature of the low temperature stage of the intermediate or bottoms product zone of next lower pressure, partially vaporized in interreboilers exchanging heat with the overhead condensing zone, and fed to the respective low temperature stage in the intermediate zone and to the bottoms product zone. Vapors from the low temperature stages in the intermediate pressure zone and from the bottoms product zone are mechanically compressed to about the pressure of the next higher pressure section or zone immediately above, generally at a temperature above that of the high temperature stage to supply reboil duty.

As the number of intermediate zones is increased, the distillation column and methodology approach approximately isothermal operation with multiple interreboiling such that the internal reflux ratio in each intermediate zone approaches the minimum to approximately the same degree. Trim heat removal at the overhead condenser is preferably provided by external refrigeration. In this manner, the distillation column and methodology uses open loop heat pumping to approach isothermal operation with optimal interreboiling, a minimal amount of heat exchange, and minimal excursions in temperature within the column. The operating temperature can be chosen to avoid expensive alloy steel construction materials, and the operating pressures are well below critical conditions and well above atmospheric pressure, thus providing economical conditions for compression. Because overhead vapors are not used for heat pumping, they risk minimal contamination by process leaks. Although isothermal operation may theoretically be approached using compression on every zone, two or three compression stages will usually be economically optimum using conventional compression equipment.

DESCRIPTION OF THE INVENTION

The present invention is generally applicable to the separation of close-boiling light hydrocarbons, particularly light hydrocarbons having positive deviations from ideal solution behavior. Representative examples include mixtures of ethylene and ethane; propylene and propane; 1-butylene and n-butane; and the like. Such separations are encountered, for example, in an olefins plant where hydrogen, methane, ethylene, propylene and higher molecular weight hydrocarbons are produced from a steam-cracked hydrocarbon feed. Ethylene-ethane and propylene-propane splitting columns are generally used after the cracked gases have been compressed and cooled by refrigeration, the methane and lighter gases have been removed, the heavier hydrocarbons have been removed, and any acetylene and diene impurities have been removed so the mixture is essentially 100% light hydrocarbon mixture. For the purposes of simplicity and clarity, reference is made hereinbelow to the separation of ethylene from ethane as a representative example, and not by way of limitation.

Figure 1:
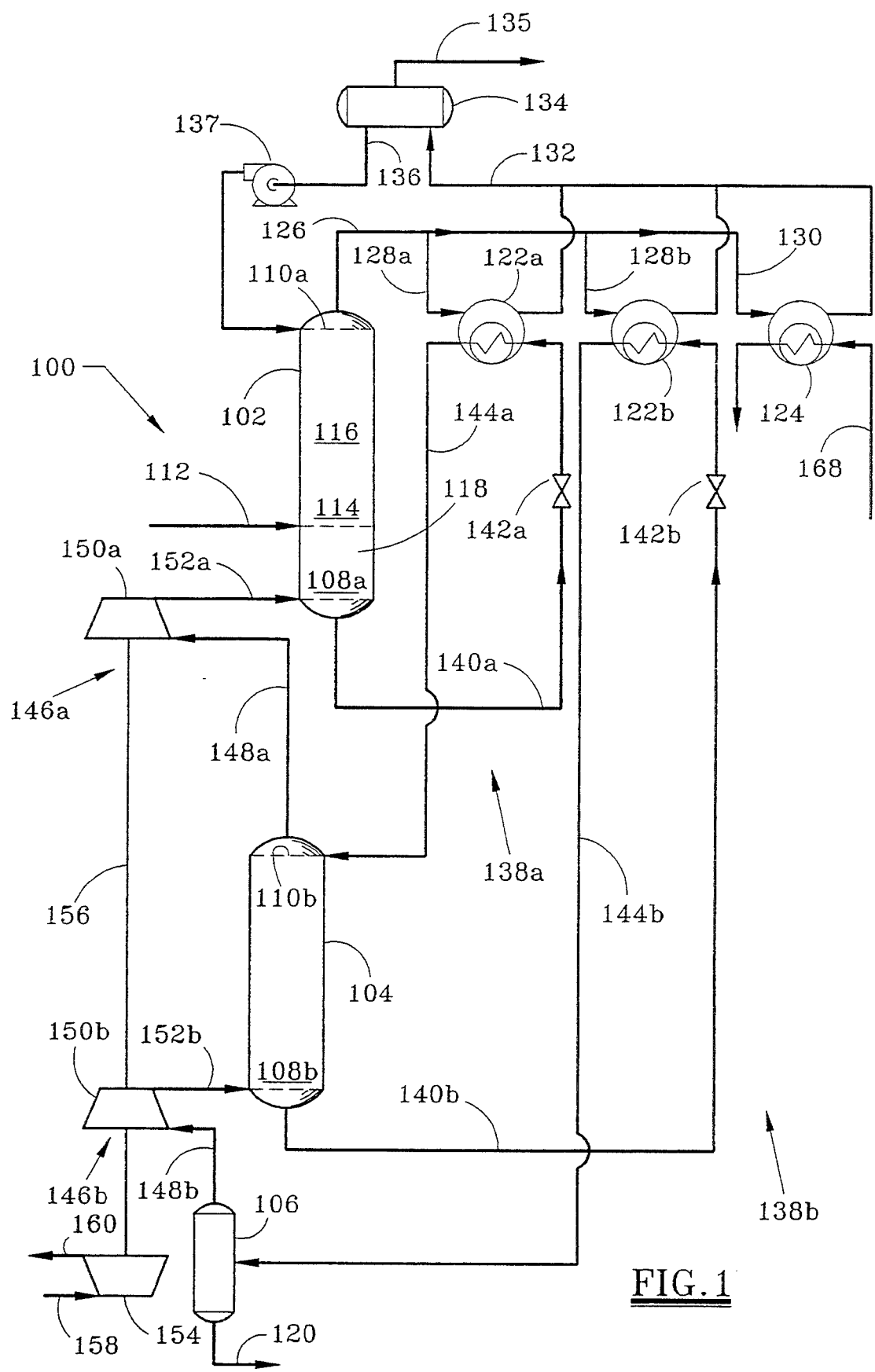
FIG. 1 is a process schematic illustrating a thermomechanically integrated distillation process and apparatus using two stages of compression according to the present invention.

With reference to the drawings, wherein correspondence in the last two digits of the reference numerals is used to indicate corresponding parts, and suffixed lower case letters are used to lo designate similar parts associated with different sections, zones or stages, the distillation unit 100 illustrated schematically in FIG. 1 is representative of one preferred embodiment of the invention employing two stages of compression. The distillation unit 100 includes high pressure section 102, an intermediate pressure zone 104 and a bottoms product zone or reboiler drum 106. The high pressure section 102 has a high temperature stage 108a adjacent a lower end thereof and a low temperature stage 110a adjacent an upper end thereof. A feed line 112 is provided for introducing an ethylene-ethane mixture into feed zone 114 dividing the section 102 into a relatively tall enriching zone 116 and a relatively short stripping zone 118. Similarly, intermediate pressure zone 104 includes a high temperature stage 108b and a low temperature stage 110b adjacent lower and upper ends thereof., respectively. The bottoms product zone 106 consists of a single stage, but if desired, could include additional separation stages. Line 120 is provided for withdrawal of a liquid for the ethane product stream.

An overhead condensing zone includes condensers 122'a–b and 124. Line 126 is provided to supply vapor from the low temperature stage 110a to condenser feed lines 128a–b and 130. A line 132 is provided for returning the cooled fluid from the condensers 122a–b and 124 to a condensate drum 134 which is connected to respective lines 135 and 136 for withdrawing vapor and liquid therefrom. If desired, the partial condensers 122a–b and 124 can be combined or made integral with the reflux drum 134. Reflux pump 137 is provided for supplying condensate from the drum 134 to the low temperature stage 110a.

Cooling loops 138a–b include coolant supply lines 140a–b from high temperature stages 108a–b to expansion valves 142a–b and condensers 122a–b, and return lines 144a–b from the condensers 122a–b to the respective low temperature stage 110b and the reboiler drum 106. An external coolant can be supplied via line 168 for trim to the condenser 124.

Compression loops 146a–b include respective lines 148a–b for supplying vapor from the low temperature stage 110b and the reboiler drum 106 to compressors 150a–b which discharge into lines 152a–b to supply the compressed fluid to the high temperature stages 108a–b of the high pressure section 102 and the intermediate pressure zone 104, respectively. Power for the compressors 150a–b can be supplied, for example, by steam turbine 154 mounted on a common driver 156. Lines 158 and 160 are provided for supplying high pressure steam to the turbine 154 and returning low pressure steam, respectively.

In operation of the FIG. 1 embodiment, a feed containing ethylene and ethane typically at saturated conditions, is introduced via line 112 into the feed zone 114. In the high pressure section 102, ethylene vapor is rectified in the relatively tall enriching zone 116 and some ethylene is stripped from the ethane in the relatively short stripping zone 118. Liquid reflux is pumped to the top of the high pressure section 102 to absorb ethane from the rising vapor. Liquid from the bottom stages 108a–b is flashed through respective valves 142a–b, partially vaporized in the parallel overhead condensers 122a–b, and injected onto the top stage 110b of the relatively small intermediate pressure zone 104 and the reboiler drum 106, respectively. Vapors from the top stage 110b of the intermediate pressure zone 104 are compressed in the compressor 150a and sent to the bottom stage 108a of the, high pressure section 102 to strip ethylene from the downcoming liquid.

The pressure of the intermediate pressure zone 104 is designed so that the temperature driving forces in the condenser 122a, usually a minimum ΔT of at least about 3° F., are economically appropriate. The duty of the condenser 122a is designed so that the internal reflux ratios in the intermediate pressure zone 104 are economically appropriate. The number of trays in the high pressure section 102 and the intermediate pressure zone 104 are designed to be economically appropriate.

Vapors from the reboiler drum 106 are compressed by compressor 150b and discharged into the bottom tray 108b to strip ethylene from the downcoming liquid in the intermediate pressure zone 104. The pressure of the reboiler drum 106 is designed so that the temperature driving forces in the condenser 122b, usually a minimum ΔT of at least about 5° F., are economically appropriate. The duty of the second parallel condenser 122b is designed so that the ethylene loss in the bottom (ethane) product line 120 is economically appropriate.

The duty of the condenser 124 is designed so that the ethane impurity in the overhead (ethylene) product meets specification. Flow splitters (not shown) are provided on the feeds 128a–b to the first two overhead condensers 122a–b so that the duties which are determined from the reboiling requirements can be satisfied. The power supplied to drive the compressor stages 146a–b generally determines the purity of the bottoms (ethane) product in line 120.

Figure 2:
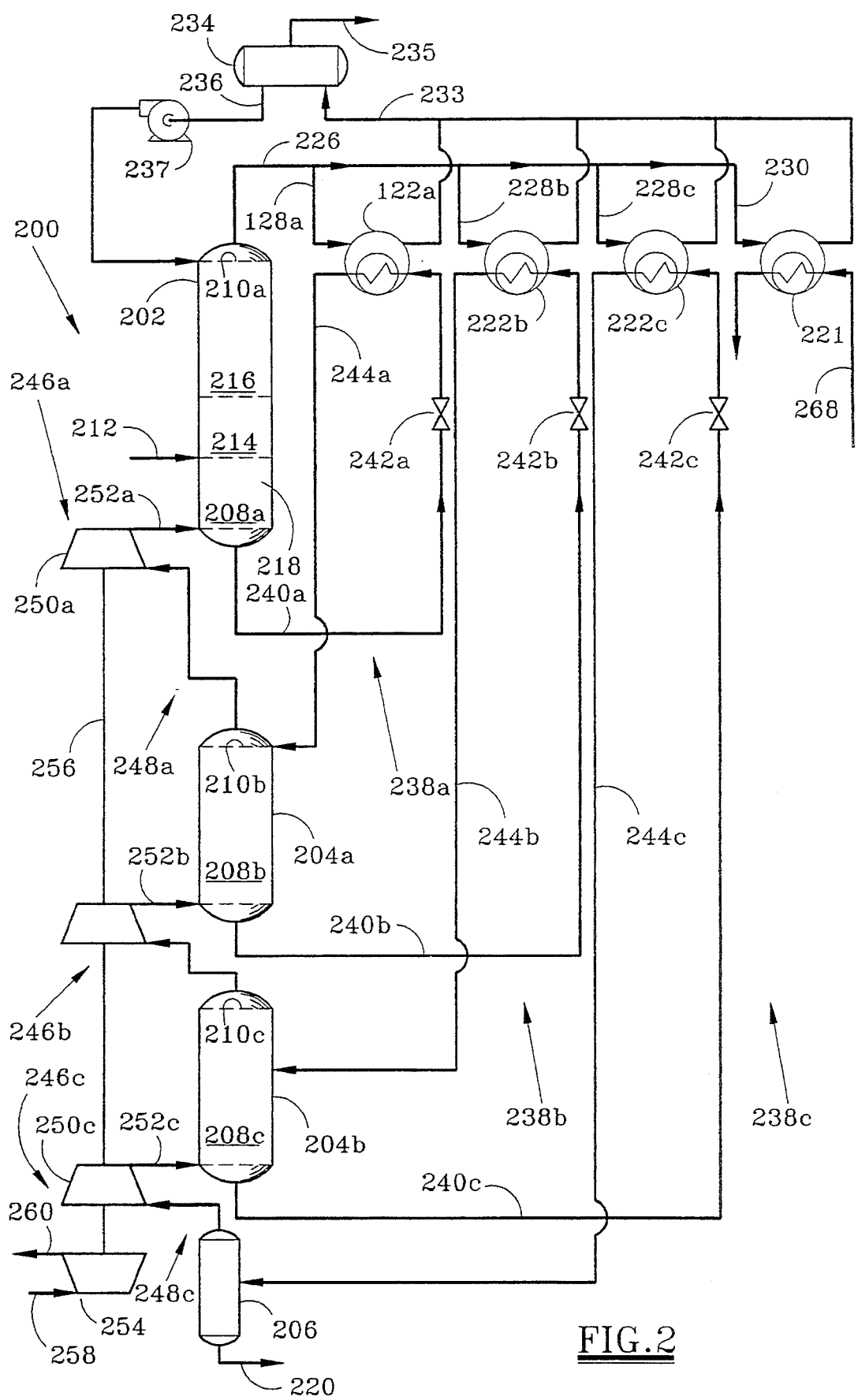
FIG. 2 is a process schematic illustrating a thermomechanically integrated distillation process and apparatus using three stages of compression according to the present invention.

FIG. 2 shows an embodiment of the invention using three stages of compression which may be more economical than two compression stages in some circumstances. Distillation unit 200 is similar to the unit 100 of FIG. 1 and corresponding components are indicated by correspondence in the last two digits of the numerical references to avoid repetition for the sake of simplicity and brevity. A fourth overhead condenser 222c, a fourth condenser feed line 228c including a flow splitter (not shown), two intermediate zones 204a–b, a third valve 242c, and a third compressor stage 246c are added to approach isothermal operation more closely. These additional features are designed in the same manner as described above to be economically appropriate, and the size and utility consumption of the overall process will be reduced at the expense of increased complexity. An even closer approach to isothermal operation with additional reductions in size and utility consumption can be similarly achieved using four or more stages of compression; however, at some point determined by economics of the specific installation, the increased capital cost due to the complexity of the process will outweigh the benefits of reduced size and utilities consumption.

Figure 3:
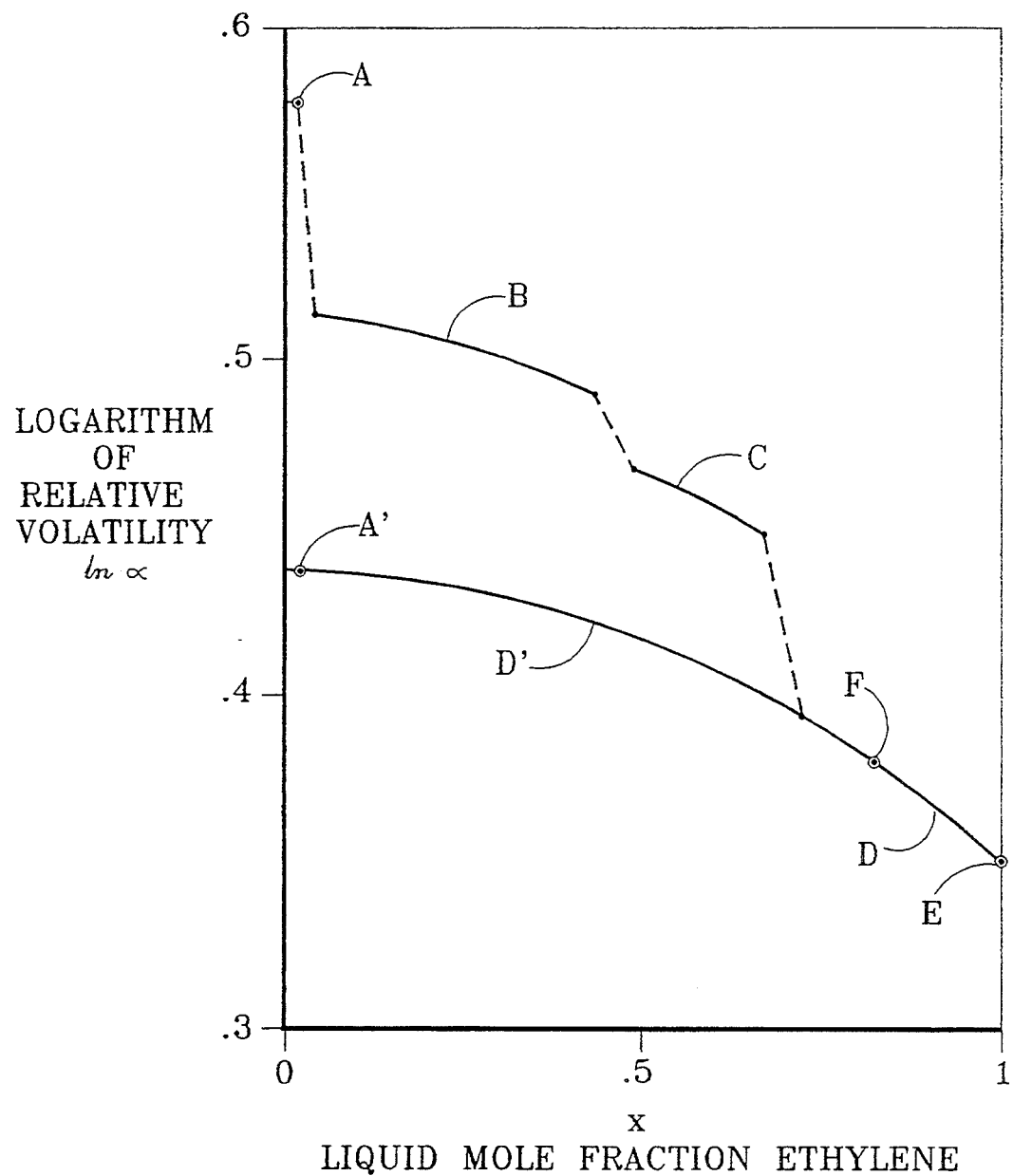
FIG. 3 graphically illustrates a comparison of the relative volatilities of ethylene to ethane according to FIG. 2 of the present invention and according to conventional distillation.

The logarithm of the relative volatility of ethylene to ethane (ln($\alpha$)) as a function of the liquid mole fraction of ethylene (x) at temperatures and pressures relevant to the operation of the FIG. 2 embodiment is illustrated graphically in FIG. 3. When the unit 200 of FIG. 2 is operated at economically advantageous conditions where the condensing temperature of the overhead vapor is approximately −30° F., point A is the ln($\alpha$) corresponding to the ethane product conditions in the reboiler drum 206, curve B to the conditions in the intermediate zone 204b, curve C to the conditions in the intermediate zone 204a, and curve D (to the right of the intersection with the dashed line) to the conditions in the high pressure section 202. Point A' and curve D' (left of the intersection with the dashed line) correspond respectively to the ethane product condition and the conditions in the lower stripping section of a conventional isobaric distillation column. Points E and F correspond respectively to the ethylene product condition and the feed condition of both the conventional isobaric column, and the high pressure section 202 of the distillation unit 200. The ln($\alpha$) in rectification in both the isobaric and unit 200 distillation is essentially the same (curve D), but is much higher in the unit 200 stripping as the pressure is reduced into the intermediate zone 204a (curve C versus curve D'), increases again as the pressure is reduced into the intermediate zone 204b (curve B versus curve D'), and is even greater in the reboiler drum 206 (point A versus point A'). Consequently, the number of separation stages is considerably reduced which in turn results in the operating and capital costs for this portion of the distillation unit 200 being significantly less than for a conventional distillation column, even when the conventional column is equipped with an interreboiler and is heat pumped.

Figure 4:
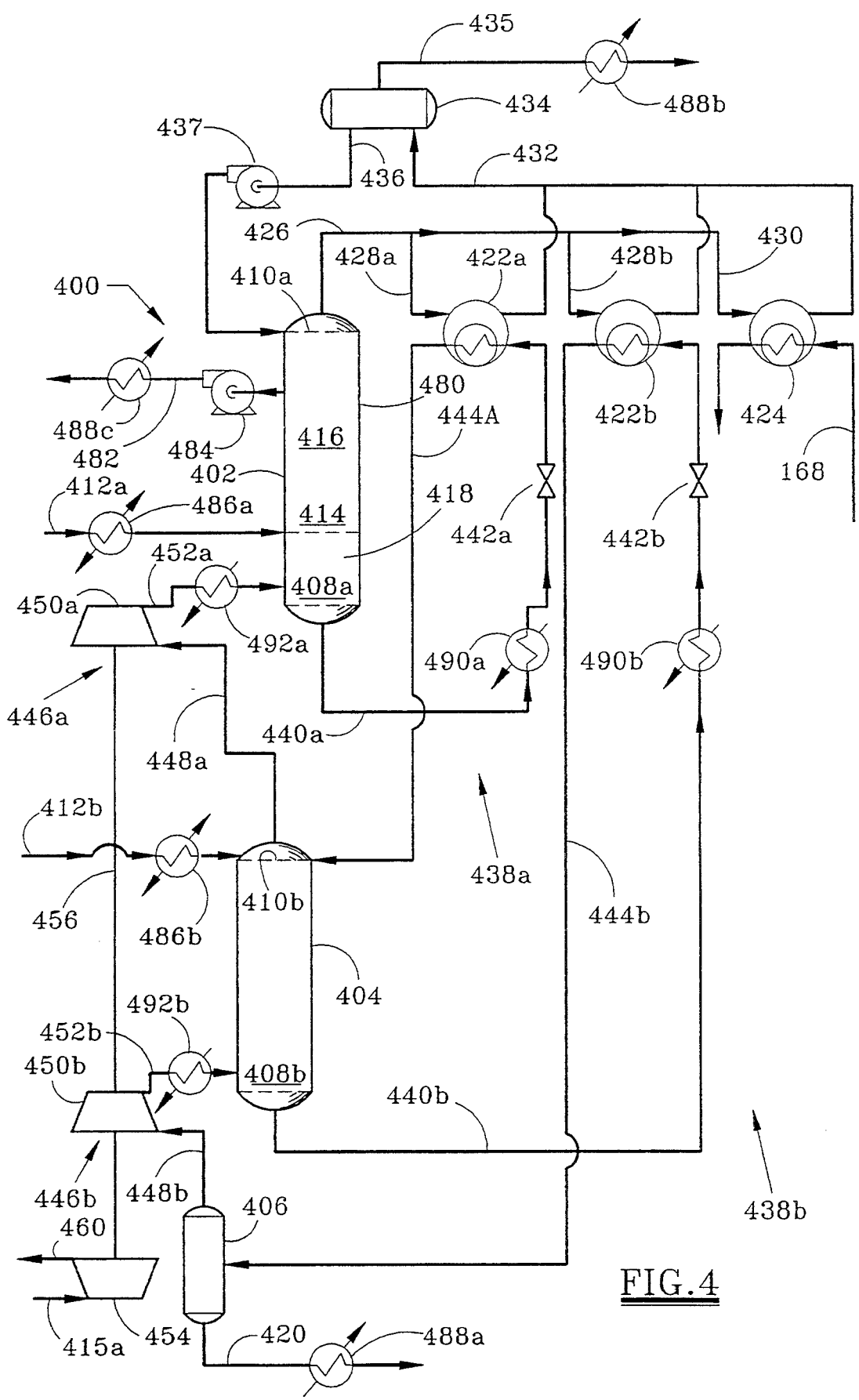
FIG. 4 is a process schematic illustrating a thermomechanically integrated distillation process and apparatus using two stages of compression according to the present invention, showing a pasteurization section, additional and/or alternate feed locations, and integration of other process streams.

FIG. 4 illustrates another embodiment incorporating a pasteurization zone, alternate or additional feed locations and process integration. Distillation unit 400 is similar to the unit 100 of FIG. 1 and corresponding components are again indicated by correspondence in the last two digits of the numerical references to avoid repetition for the sake of simplicity and brevity. The unit 400 includes a pasteurization zone 480 which facilitates purging small amounts of relatively volatile impurities such as methane, carbon monoxide or the like together with some ethylene in the overhead vapor stream 435 from the drum 434. The ethylene product is withdrawn as a liquid side-draw via line 482 and pump 484. The take-off for line 482 is several stages below the low temperature stage 410a.

The feed to the unit 400 is introduced via line 412a or alternatively or additionally via line 412b to the intermediate pressure zone 404. The location and number of feeds are determined by economics of the specific installation. Generally, a particular feed is introduced at a stage having about the same pressure, temperature, composition and quality as the feed.

Process integration can also be used to further enhance the energy requirements of the distillation unit 400 and the overall process of which it is a part, e.g. in an olefins plant. For example, the feed streams 412a–b can be heated or cooled in respective exchangers 486a–b. Examples of heating media for such heat exchange include refrigerant subcooling, distillation condensers and the like; examples of cooling media include refrigerant streams, distillation column reboilers and the like. Similarly, the product streams 420, 435 and 482 can be heated in the; respective exchangers 488a–c; the liquids in lines 440a–b from the high temperature stages 408a–b can be subcooled in exchangers, 490a–b before expansion across the valves 442a–b; and the superheated compressed vapors in lines 452a–b can be desuperheated in exchangers 492a–b before discharge into the high temperature stages 408a–b.

The specific design of the equipment varies from installation to installation, depending on various economic and environmental circumstances, as is well known by the skilled artisan. Typical materials of construction are normally used, such as, for example, mild steel at temperatures down to 18° F., killed steels at process temperatures to as low as about −45° F., etc. In the preferred embodiment of the present invention, temperatures below about −45° F. are avoided so that requirements for stainless steel and more expensive alloys are largely eliminated.

The design and sizing of the columns used in the present invention can be based on typical tray and structural characteristics for conventional fractionation equipment. As one example, killed steel or carbon steel double pass cascade sieve trays can have the following characteristics:

| | |
|---|---|
| Hole diameter | 0.375 in. |
| Triangular pitch | (2.5)(0.375) in. |
| Active area | 85% |
| Plate thickness | 1.33 in. |
| Tray spacing | 24 in. |
| Tray efficiency | 87% |
| Superficial velocity | 85% of flooding velocity |

The column diameter can be estimated using commercially available software such as ASPEN PLUS, or can be calculated from regressed correlation, such as in Haddad, H., "The Optimization of Ethylene/Ethane Distillation," A Thesis, The University of Missouri—Rolla, 1989. The shell thickness, windloading, and the column design parameters are designed based on generally accepted engineering principles, such as, for example, as described in Siemon, *Manual for Design of Ferrous and Nonferrous Pressure Vessels*, 3rd Edition, Edwards Brothers, 1944; Bednar, *Pressure Vessel Design Handbook*, Van Nostrand Reinhold, 1989; and the like.

The compressors used in the present invention are similarly designed and sized using conventional methodology. For example, the individual compressor blocks can be simulated, using commercial simulation software such as that available under the trade designation ASPEN PLUS, to model each stage of a multistage compressor. Similarly, heat exchanger surface area calculations are within the ordinary skill in the art, for example, by using commercially available software, such as is available under the trade designation ASPEN PLUS. Single pass shell and bonnet type heads are generally suitable.

Methods for equipment cost estimations such as for the columns, compressors, heat exchangers and flash drums are well known in the art, as are methods for estimating energy consumption, primarily compressor work, energies of the feed, products, and refrigeration heat sinks, cooling water, and the like. Economic evaluations, and process optimizations are generally specific to the particular installation conditions, economic conditions and practitioner preference, and representative examples are described in detail in Greene, Dominic G., "Thermomechanically Integrated Distillation of Ethylene from Ethane," A Thesis, The University of Missouri-Rolla, Presented 1992 (Unpublished), which is hereby incorporated herein by reference in its entirety, a copy of which appears in the Patent and Trademark Office patent file or records.

The invention is further illustrated in the following examples.

EXAMPLE 1

The two-stage embodiment of FIG. 1 was simulated for the separation of a hydrocarbon mixture containing essentially 100 weight percent ethylene and ethane. In this example, it is desired to separate ethylene of 99.9 mole percent purity and ethane of 99.0 mole percent purity from a starting mixture of 5104 lb-mole/hr containing 80 mole percent ethylene and 20 mole percent ethane at a temperature of −30.2° C. (−22.3° F.), a pressure of 1.7 MPa (250 psia), and a vapor mole fraction of 0.8. The feed mixture is introduced to the high pressure section 102 which contains 73 theoretical separation stages in an enriching zone above the feed stage, and 5 theoretical separation stages in a high pressure stripping zone below the feed stage. Overhead vapor (16,712 lb-mole/hr) from the high pressure section 102 at a temperature of −31.2° F. and a pressure of 242.8 psia is divided into the lines 128a–b and 130, and partially condensed in the respective heat exchangers 122a–b and 124. The exchanger 122a has a duty of 26.7×10$^6$ Btu/hr, the exchanger 122b 19.303×10$^6$ Btu/hr, and the exchanger 124 6.638×10$^6$ Btu/hr. The partially condensed streams are fed to the reflux drum 134 at a temperature of −32.0° F. and pressure of 239.8 psia for separation into 4077 lb-mol/hr of vapor ethylene product in line 135 of 99.9 mole percent purity, and 12,635 lb-mole/hr of liquid reflux in line 136.

Liquid from the bottom stage 108a of the high pressure section 102 is flashed at 12,460 lb-mole/hr from a temperature of −16.5° F. and a pressure of 250.5 psia, through the valve 142a to a pressure of 174.8 psia, partially vaporized in the exchanger 122a to a vapor mole fraction of 0.5554, and fed to the top stage 110b of intermediate zone 104 for mixing with the rising vapor and for phase separation. Overhead vapor from the top stage 110b of the intermediate zone 104 at a temperature of −36.9° F. and a pressure of 174.3 psia is compressed at a rate of 11,433 lb-mole/hr in the compressor 150a to a pressure of 250.5 psia and a temperature of 6.2° F. and fed to the bottom stage 108a of the high pressure section 102 to strip ethylene from the falling liquid. The power requirement of the high pressure compressor stage is 1,560 BHP.

TABLE 1A

| Stream (FIG. 1) | Flow Rate (lb-mole/hr) | Pressure (psia) | Temp. (°F.) | Vapor Mole Fraction | Ethylene Mole Fraction |
|---|---|---|---|---|---|
| Feed (112) | 5,104 | 250.0 | −22.3 | 0.8000 | 0.8005 |
| Overhead Vapor (126) | 16,712 | 242.8 | −31.2 | 1.0000 | 0.9987 |
| Ethylene Product (135) | 4,077 | 239.8 | −32.0 | 1.0000 | 0.9990 |
| Reflux (136) | 12,635 | 242.8 | −32.0 | 0.0000 | 0.9986 |
| HP Section Bottoms | 12,460 | 250.5 | −16.5 | 0.0000 | 0.5703 |

TABLE 1A-continued

| Stream (FIG. 1) | Flow Rate (lb-mole/hr) | Pressure (psia) | Temp. (°F.) | Vapor Mole Fraction | Ethylene Mole Fraction |
|---|---|---|---|---|---|
| (140a) Interm. Zone Reflux | 12,460 | 174.3 | −37.0 | 0.5554 | 0.5703 |
| (144a) Interm. Zone Vapor | 11,433 | 174.3 | −36.9 | 1.0000 | 0.3794 |
| (148a) HP Compressor Return | 11,433 | 250.5 | +6.2 | 1.0000 | 0.3794 |
| (152a) Interm. Zone Bottom | 5,157 | 176.3 | −14.9 | 0.0000 | 0.0165 |
| (140b) Reboiler Drum Feed | 5,157 | 120.4 | −37.0 | 00.8009 | 0.0165 |
| (144b) Reboiler Drum Vapor | 4,130 | 120.4 | −37.0 | 1.0000 | 0.9819 |
| (148b) Intermediate Compressor Return | 4,130 | 176.3 | +4.5 | 1.0000 | 0.9819 |
| (152b) Ethane Product (120) | 1,027 | 120.4 | −37.0 | 0.0000 | 0.0100 |

The intermediate section 104 contains 21 theoretical separation stages. Liquid from the bottom stage 108b of the intermediate section 104 at a temperature of −14.9° F. and a pressure of 176.3 psia is withdrawn at a rate of 5157 lb-mole/hr, flashed through the valve 142b to a pressure, of 120.9 psia and a temperature of −37.0° F., partially vaporized in the exchanger 122b to a vapor mole fraction of 0.8009, and fed to the reboiler drum 106 at a pressure of 120.4 psia and a temperature of −37.0° F. for phase separation into 1,027 lb-mole/hr of liquid ethane product in line 166 of 99.0 mole percent purity and 4130 lb-mole/hr of vapor in line 148b. The vapor from line 148b is compressed in compressor 150b to a pressure of 176.3 psia and a temperature of 4.5° F. The power requirement of the compressor 150b is 615 HP. The compressed vapor is returned via line 152b to the low pressure section 104 to strip ethylene from the falling liquid.

The simulation results are tabulated in Tables 1A, 1B and 1C.

TABLE 1B

| Heat Exchanger (FIG. 1) | Duty ($10^6$ Btu/hr) |
|---|---|
| HP Condenser (122a) | 26.700 |
| Intermediate Condenser (122b) | 19.303 |
| External Refrigerant (124) | 6.638 |

TABLE 1C

| Compressor | BHP |
|---|---|
| High Pressure (150a) | 1560 |
| Intermediate Pressure (150b) | 615 |

EXAMPLE 2

The process-integrated embodiment of FIG. 4 was simulated for the separation of two feed streams containing ethylene and ethane into ethylene and .ethane product streams of the same purity as in Example 1. The first feed stream 412a is 5154.0 lb-mole/hr containing 84.97 mole percentethylene,.14.99 mole percent ethane, 0.0014 mole percent carbon monoxide and 0.0363 mole percent methane, at a temperature of 100° F., a pressure of 353.0 psia, and a vapor mole fraction of 1.0. The second feed stream 412b is 100.0 lb-mole/hr of liquid containing 24.35 mole percent ethylene and 75.65 mole percent ethane at a temperature of 39.6° F. and a pressure of 450.0 psia.

The first feed stream 412a is passed through heat exchanger 486a where it is cooled against a stream of ethane and ethylene to a temperature of −1.6° F. and a vapor mole fraction of 1.0, and then fed to the high pressure section 402 containing 90 theoretical separation stages in an enriching zone above the feed stage, and 15 theoretical separation stages below the feed stage. The second feed 412b is passed through heat exchanger 486b where it is cooled against a stream of ethylene to a temperature of −10° F. and a vapor mole fraction of 0.0, and then fed to the intermediate pressure section 404 containing 12 theoretical separation stages above the feed stage, and 14 theoretical separation stages below the feed stage.

Overhead vapor (19032.7 lb-mole/hr) from the high pressure section 402 at a temperature of −10.5° F. and a pressure of 341.0 psia is divided into the lines 428a–b and 430 and condensed in the respective heat exchangers 422a–b and 424. The exchanger 428a has a duty of $34.686 \times 10^6$ Btu/hr, the exchanger 428b $13.114 \times 10^6$ Btu/hr, and the exchanger 430 $21.441 \times 10^6$ Btu/hr. The condensed streams are fed to the reflux drum 434 at a temperature of −13.0° F. and 338.0 psia. An overhead purge of 54.2 lb-mole/hr of 0.13 mole percent carbon monoxide, 3.17 mole percent methane and 96.70 mole percent ethylene is taken off continuously or intermittently via line 435. For recovery of refrigeration, the stream 435 is heated in heat exchanger 488a ($0.072 \times 10^6$ Btu/hr) against propylene refrigerant. Liquid is refluxed at 18978.5 lb-mole/hr via line 436 and pump 437 to the low temperature stage 410a. A side-draw 482 of 4347.2 lb-mole/hr of liquid ethylene product of 99.9 mole percent purity is pumped via pump 484 through heat exchanger 488c ($7.650 \times 10^6$ Btu/hr) where it is heated for recovery of refrigeration against propylene refrigerant.

Liquid (13982.5 lb-mole/hr) from the bottom stage 408a of the high pressure section 402 is subcooled in heat exchanger 490a ($7.239 \times 10^6$ Btu/hr) against propylene refrigerant to a temperature of −10.3° F., flashed through the valve 442a to a pressure of 222.3 psia, vaporized in the exchanger 422a to a vapor mole fraction of 0.6077, and fed to the top stage 410b of intermediate zone 404 for mixing with the rising vapor and phase separation. Overhead vapor from the top stage 410b of the intermediate zone 404 at a temperature of −18.3° F., and a pressure of 221.8 psia is compressed at a rate of 13229.9 lb-mole/hr in the compressor 450a to a pressure of 354.5 psia, desuperheated in the heat exchanger 492a (4.437×10⁶ Btu/hr) against propylene refrigerant to a temperature of 18.0° F., and fed to the bottom stage 408a of the high pressure section 402 to strip ethylene from the falling liquid. The power requirement of the high pressure compressor stage 446a is 2268.1 BHP.

Liquid from the bottom stage 408b of the intermediate section 404 at a temperature of 0.3° F and a pressure of 224.4 psia is withdrawn at a rate of 3840.8 lb-mole/hr, subcooled in heat exchanger 490b (1.200×10⁶ Btu/hr) against propylene refrigerant, flashed through the valve 442b to a pressure of 159.7 psia and a temperature of −21.0° F., partially vaporized in the exchanger 422b to a vapor mole fraction of 0.7157, and fed to the reboiler drum 406 at a pressure of 159.1 psia and a temperature of −21.0° F. for phase separation into 852.6 lb-mole/hr of liquid ethane product in line 420 of 99.0 mole percent purity and 2988.2 lb-mole/hr of vapor in line 448b. Product stream 420 is heated in heat exchanger 488b (4.284×10⁶ Btu/hr) against propylene refrigerant to a temperature of −20.8° F. The vapor from line 448b is compressed in compressor 450b to a pressure of 227.4 psia, desuperheated in heat exchanger 492b (0.458×10⁶ Btu/hr) against propylene refrigerant to a temperature of 8.3° F., and fed to the bottom stage 408b in the intermediate pressure section 404 to strip ethylene from the falling liquid. The power requirement of the compressor 450b is 406.8 BHP.

The simulation results are tabulated in Tables 2A, 2A and 2C.

TABLE 2A

| Stream (FIG. 4) | Flow Rate (lb-mole/hr) | Pressure (psia) | Temp. (°F.) | Vapor Mole Fraction | Ethylene Mole Fraction |
|---|---|---|---|---|---|
| 1st Feed (412a) | 5154.0 | 353.0 | 100.0 | 1.0000 | 0.8497 |
| 2nd Feed (412b) | 100.0 | 450.0 | 39.6 | 0.0000 | 0.2435 |
| Overhead Vapor (426) | 19032.7 | 341.0 | −10.5 | 1.0000 | 0.9908 |
| Purge Stream (435) | 54.2 | 338.0 | −13.0 | 1.0000 | 0.9670 |
| Ethylene Product (482) | 4347.2 | 341.8 | −9.5 | 0.0000 | 0.9990 |
| Reflux (436) | 18978.5 | 338.0 | −13.0 | 0.0000 | 0.9909 |
| HP Bottoms (440a) | 13982.5 | 351.5 | 10.0 | 0.0000 | 0.4937 |
| Interm. Zone Reflux (444a)) | 13982.5 | 221.8 | −18.8 | 0.6077 | 0.4937 |
| Interm. Zone Vapor (448a) | 13229.9 | 221.8 | −18.3 | 1.0000 | 0.5230 |
| HP Compressor Return (452a) | 13229.9 | 354.5 | 40.3 | 1.0000 | 0.5230 |
| Interm. Zone Bottoms (440b) | 3840.8 | 224.4 | 0.3 | 0.0000 | 0.0152 |
| Reboiler Drum Feed (444b) | 3840.8 | 159.2 | −20.9 | 0.7157 | 0.0152 |
| Reboiler Drum Vapor (448b) | 2988.2 | 159.1 | −21.0 | 1.0000 | 0.0167 |
| Interm. Compressor Return (452b) | 2988.2 | 227.4 | 19.7 | 1.0000 | 0.0167 |
| Ethane Product (420) | 852.6 | 159.1 | −21.0 | 0.0000 | 0.0100 |

TABLE 2B

| Heat Exchanger (FIG. 1) | Duty (10⁶ Btu/hr) |
|---|---|
| 1st Feed Heater/Cooler (486a) | 7.095 |
| 2nd Feed Heater/Cooler (486b) | 0.134 |
| Purge Stream Exchanger (488a) | 0.072 |
| Ethane Product Exchanger(488b) | 4.284 |
| Ethylene Product Exchanger(488c) | 7.650 |
| HP Liquid Subcooler (490a) | 7.239 |

TABLE 2B-continued

| Heat Exchanger (FIG. 1) | Duty (10⁶ Btu/hr) |
|---|---|
| Intermediate Pressure Liquid Subcooler (490b) | 1.200 |
| HP Desuperheater (492a) | 4.437 |
| Intermediate Pressure Desuperheater (492b) | 0.458 |
| HP Condenser (422a) | 34.686 |
| Intermediate Condenser (422b) | 13.114 |
| External Refrigerant (424) | 21.441 |

TABLE 2C

| Compressor | BHP |
|---|---|
| High Pressure (446a) | 2268.1 |
| Intermediate Pressure (446b) | 406.8 |

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

We claim:

1. Distillation apparatus for separating close-boiling light hydrocarbons selected from ethylene/ethane, propylene/propane and 1-butylene/n-butane mixtures, comprising:

a high pressure section at subcritical pressure having high and low temperature stages;

a bottoms product zone at superatmospheric pressure;

an intermediate section comprising one or more intermediate zones of successively lower pressure from the high pressure section to the bottoms product zone;

high and low temperature stages in each of the intermediate zones;

a feed zone in fluid communication with at least one of the sections for receiving a mixture of hydrocarbons including a light component and a heavy component;

an overhead condensing zone adjacent the low temperature stage of the high pressure section for condensing the light component at a condensation temperature;

a plurality of cooling loops, each loop including an expansion valve for flashing fluid from a respective high temperature stage into a respective coolant supply line below the condensation temperature through the condensing zone and into respective coolant return lines for introducing fluid of similar pressure into the low temperature stage of each respective intermediate zone and the bottoms product zone, wherein at least one of the cooling loops flashes fluid from the high temperature stage of one of the intermediate zones;

a plurality of compression loops for compressing fluid from the respective bottoms product zone and the low temperature stage of each intermediate zone, and discharging the compressed fluid to a respective high temperature stage of similar pressure;

a line for taking off light-component product of reduced heavy-component content from adjacent the condensing zone;

a line for taking off heavy-component product of reduced light-component content from the bottoms product zone.

2. The apparatus of claim 1, wherein the feed zone is adjacent the high temperature stage of the high pressure section.

3. The apparatus of claim 2, including a stripping stage interposed between the feed zone and the high temperature stage of the high pressure section.

4. The apparatus of claim 1, wherein the feed zone is adjacent the low temperature stage of the intermediate zone having the highest pressure.

5. The apparatus of claim 1, further including a cooling loop for controllably circulating an external coolant through the condensing zone.

6. The apparatus of claim 1, wherein the intermediate section consists of one intermediate zone.

7. The apparatus of claim 1, wherein the intermediate section consists of two intermediate zones.

8. The apparatus of claim 1, wherein the plurality of cooling loops flash liquid from the high temperature stages and return vapor to the low temperature stages and the bottoms product zone.

9. The apparatus of claim 1, wherein the plurality of compression loops compress vapor from the bottoms product zone and the high temperature stages of the intermediate zone or zones.

10. The apparatus of claim 1, wherein the light-component product line is a side-draw at least two theoretical stages below a take-off line from a pasteurization zone for removing components more volatile than the light-component product.

11. A method for separating close-boiling light hydrocarbons selected from ethylene/ethane, propylene/propane and 1-butylene/n-butane mixtures by fractional distillation, comprising the steps of:

(a) supplying a mixture of hydrocarbons to a feed zone of a distillation unit having a high pressure section at subcritical pressure, an intermediate section including one or more intermediate zones of successively lower pressure from the high pressure section to a bottoms product zone at superatmospheric pressure, wherein the sections each have high and low temperature stages and the high pressure section has an overhead condensing zone adjacent the low temperature stage thereof;

(b) condensing a light component in the condensing zone in heat exchange against a plurality of cooler fluid streams expanded from the high temperature stages, including at least one stream expanded from a high temperature stage of one of the intermediate zones;

(c) introducing the expanded fluid streams from step (b) to the respective low temperature stage in the intermediate zone or zones and the bottoms product zone having about the same pressure as the respective fluid stream from step (b);

(d) compressing fluid streams from the bottoms product zone and the low temperature stage of each intermediate zone;

(e) introducing the compressed fluid streams from step (d) to the respective high temperature stages in the intermediate and high pressure sections having about the same pressure as the respective compressed fluid stream from step (d);

(f) recovering a light-component stream adjacent the condensing zone having a reduced heavy-component content; and (g) recovering a heavy-component stream adjacent the bottoms product zone having a reduced light-component content.

12. The method of claim 11, wherein the feed zone is adjacent the high temperature stage of the high pressure section.

13. The method of claim 12, wherein the high pressure section includes a stripping stage interposed between the feed zone and the high temperature stage of the high pressure section.

14. The method of claim 1, wherein the feed zone is adjacent the low temperature stage of the intermediate zone receiving fluid expanded from the high temperature stage of the high pressure section.

15. The method of claim 11, further including condensing a portion of the light component in controllable heat exchange against an external coolant.

16. The method of claim 11, wherein the intermediate section consists of one intermediate zone.

17. The method of claim 11, wherein the intermediate section consists of two intermediate zones.

18. The method of claim 11, wherein the fluid streams expanded in step (b) comprise liquid and the fluid streams introduced in step (c) comprise vapor.

19. The method of claim 11, wherein the fluid streams compressed in step (d) comprise vapor.

20. The method of claim 11, wherein the light component is ethylene and the heavy component is ethane.

21. The method of claim 11, wherein the light component is propylene and the heavy component is propane.

22. The method of claim 11, wherein the light component is 1-butylene and the heavy component is n-butane.

23. The method of claim 11, wherein the hydrocarbon mixture includes a minor amount of a volatile component, and the method includes the further steps of recovering the light component stream in step (f) as a side-draw and removing the volatile component from a pasteurizing zone two or more theoretical stages above the side-draw.

* * * * *